United States Patent [19]

Croce et al.

[11] Patent Number: 5,506,106
[45] Date of Patent: Apr. 9, 1996

[54] METHODS OF DETECTING MICROMETASTASIS OF PROSTATE CANCER

[75] Inventors: Carlo Croce, Philadelphia, Pa.; Leonard Gomella, Sewell, N.J.; S. Grant Mulholland, Gladwynne, Pa.; Jose G. Moreno, Wayne, Pa.; Rainer Fischer, Aachen-Leniers, Germany

[73] Assignee: Thomas Jefferson University, Philadelphia, Pa.

[21] Appl. No.: 294,611

[22] Filed: Aug. 23, 1994

Related U.S. Application Data

[63] Continuation of Ser. No. 973,322, Oct. 29, 1992, abandoned.

[51] Int. Cl.$^6$ .......................... C07H 21/02; C07H 21/04; C12P 19/34; C12Q 1/68
[52] U.S. Cl. .......................... 435/6; 435/91.1; 435/91.2; 536/23.1; 536/23.2; 536/24.33; 935/77; 935/78
[58] Field of Search .......................... 435/6, 91.1, 91.2; 536/23.1, 23.2, 24.33; 935/77, 78

[56] References Cited

U.S. PATENT DOCUMENTS

| | | | |
|---|---|---|---|
| 4,446,122 | 5/1984 | Chu et al. | 424/1.1 |
| 4,803,169 | 2/1989 | Linsley et al. | 435/7 |
| 5,085,983 | 2/1992 | Scanlon | 438/6 |
| 5,153,118 | 10/1992 | Wright, Jr. et al. | 435/7.23 |

FOREIGN PATENT DOCUMENTS

| | | |
|---|---|---|
| 0520794A1 | 6/1992 | European Pat. Off. |
| WO90/02203 | 3/1990 | WIPO |

OTHER PUBLICATIONS

O'Garra et al. Current opinion in immunology 4:211–215 (1992).
Mattano et al. Sensitive Detection of Rare Circulating Neuroblastoma Cells by the Reverse Transcriptase–Polymerase Chain Reaction *Cancer Res* 1992 52:4701–4705.
Naito et al. Detection of Tyrosine Hydroxylase mRNA and Minimal Neuroblastoma Cells by the Reverse Transcription–Polymerase Chain Reaction *Euro J. Cancer* 1991 27:765–770.
Sharief et al. Human Prostatic Acid Phosphatase: cDNA Cloning, Gene Mapping and Protein Sequence Homology with Lysosomal Acid Phosphatase *Biochem Biophys Res Commun* 1989 160:79–86.
Smith et al. Detection of melanoma cells in peripheral blood by means of reverse transcriptase and polymerase chain reaction *The Lancet* 1991 338:1227–1229.
Yokota et al. Use of Polymerase Chain Reactions to Monitor Minimal Residual Disease in Acute Lymphoblastic Leukemia Patients *Blood* 1991 77:331–339.
Boring et al. Cancer Statistics, 1991, CA–A *Cancer Journal for Clinicians* 1991 41:19–36.
Byar et al. Carcinoma of the prostrate: Prognostic Evaluation of Certain Pathologic Features in 208 Radical Prostatectomies *Cancer* 1972 30:5–13.
Winter C. The Problem of Rectal Involvement by Prostatic Cancer *Surg. Gynecol. Obstet* 1957 105:136–140.
Hilaris et al. Radiation Therapy and Pelvic Node Dissection in the management of Cancer of the Prostate *Am. J. Roentgenol.* 1974 121:832–838.
McLaughlin et al. Prostatic Carcinoma: Incidence and Location of Unsuspected Lymphatic Metastases *J. Urol.* 1976 115:89–94.

(List continued on next page.)

*Primary Examiner*—W. Gary Jones
*Assistant Examiner*—Paul B. Tran
*Attorney, Agent, or Firm*—Woodcock Washburn Kurtz Mackiewicz & Norris

[57] ABSTRACT

A method of diagnosing prostate metastasis is provided by the present invention whereby RNA from a patient's blood is isolated and amplified using a pair of primers which are complementary to regions of the prostate specific antigen gene. The presence or absence of amplified RNA is detected and the presence of amplified RNA is indicative micrometastasis of prostate cancer.

4 Claims, 1 Drawing Sheet

OTHER PUBLICATIONS

Jacobs S. Spread of Prostatic Cancer to Bone *Urology* 1983 21:337–344.

Batson O. The Function of the Vertebral Veins and Their Role in the Spread of Metastases *Ann. Surg.* 1940 112:138–149.

Saitoh et al. Metastatic Patterns of Prostatic Cancer Correlation Between Sites and Number of Organs Involved *Cancer* 1984 54:3078–3084.

Whitmore W. The Natural History of Prostatic Cancer *Cancer* 1973 32:1104–1112.

Fidler et al. Biological Diversity in metastatic Neoplasms: Origins and Implications *Science* 1982 217:998–1001.

Liotta et al. Quantitiative Relationships of Intravascular Tumor Cells, Tumor Vessels, and Pulmonary Metastases following Tumor Implantation *Cancer Res.* 1974 34:997–1004.

Schirrmacher B. Cancer Metastasis: Experimental Approaches, theoretical Concepts, and Impacts for Treatment Strategies *Adv. Cancer Res.* 1985 43:1–73.

Wu et al. Detection of Micrometastases in Breast Cancer by the Polymerase Chain Reaction: A Feasibility Study *Lab. Inv.* 1990 62:109A.

Miyamura et al. Detection of Philadelphia Chromosome–Positive Acute Lymphoblastic Leukemia by Polymerase Chain Reaction: Possible Eradication of Minimal Residual Disease by Marrow Transplantation *Blood* 1992 79:1366–1370.

Stamey et al. Prostate Specific Antigen in the Diagnosis and Treatment of Adenocarcinoma of the Prostate II. Radical Prostatectomy Treated Patients *J. Urol.* 1989 141:1076–1083.

Ben–Ezra et al. Effect of Fixation on the Amplification of Nucleic Acids from paraffin–embedded Material by the Polymerase Chain Reaction *J. Histochem Cytochem.* 1991 39:351–354.

Hamdy et al. Circulating Prostate Specific Antigen–positive Cells Correlate with metastatic Prostate Cancer *Br. J. Urol.* 1992 69:392–396.

Harty et al. In Vitro Technique for Isolating Prostatic Cells from Blood *J. Surg. Res.* 1979 26:411–416.

Henttu et al. cDNA Coding for the Entire Human Prostate Specific Antigen Shows High Homologies to the Human Tissue Kallikrein Gens *Biochem. Biophys. Res. Comm.* 1989 160:903–910.

Watt et al. Human prostate–specific antigen: Structural and functional similarity with serine proteases *Proc. Natl. Acad. Sci. USA* 1986 83:3166–3170.

Lilja H. A Kalibrein–like Serine Protease in Prostatic Fluid Cleaves the Predominant Seminal Vesicle Protein *J. Clin. Invest.* 1985 76:1899–1903.

Lundwall et al. Molecular cloning of human prostate specific antigen cDNA *FEBS letters* 1987 214(2):317–322.

Henttu et al. Expression Of The Gene Coding For Human Prostate–Specific Antigen and Related hGK–1 In Benign and malignant Tumors of The Human Prostate *Int. J. Cancer* 1990 45:654–660.

Riegman et al. Molecular Cloning and Characterization of novel Prostate Antigen cDNA's *Biochem. Biophys. Res. Comm.* 1988 155:181–188.

Christensson et al. Serum Prostate Specific Antigen Complexed to $\alpha 1$–Antichymotrypsin as an Indicator of Prostate Cancer *J. Urology* 1993 150:100–105.

Barak et al. Binding of Serum Prostate Antigen to Concanavalin A in Patients with Cancer of Hyperplasia of the Prostate *Oncology* 1989 46:375–377.

Moreno et al. Detection of Hematogenous Micrometastasis in Patients with Prostate Cancer *Cancer Res.* 1992 52:6110–6112 published Oct. 27, 1992.

Goblet et al. One–step amplification of transcripts in total RNA using the polymerase chain reaction *Nucleic Acid Res.* 1989 17:2144.

Riegman et al. Characterization of the Prostate–Specific Antigen Gene: A Novel Human Kallikrein–Like Gene *Biochem. Biophys. Res. Comm.* 1989 159:95–102.

METHODS OF DETECTING MICROMETASTASIS OF PROSTATE CANCER

This is a continuation of application Ser. No. 7/973,322, filed Oct. 9, 1992 now abandoned.

FIELD OF THE INVENTION

This invention is directed to methods of detecting prostate cancer micrometastasis.

BACKGROUND OF THE INVENTION

Prostate cancer metastasis will claim the lives of over 30,000 Americans this year. Boring et al., *Cancer Statistics* 1991, 19. The mode of dissemination however, remains very poorly understood. An almost dogmatic view of metastasis holds that prostate cancer cells first spread through the prostatic capsule then into the lymphatics, and eventually hematogenously travel to bone. Byar et al., *Cancer* 1972, 30, 5; Winter, C. C., *Surg. Gynecol. Obstet.* 1957, 105, 136; Hilaris et al., *Am. J. Roentgenol.* 1974, 121, 832; McLaughlin et al., *J. Urol.* 1976, 115, 89; Jacobs, S. C., *Urology* 1983, 21, 337; Batson, O. V., *Ann. Surg.* 1940, 112,138; Saitoh et al., *Cancer* 1984, 54, 3078–3084; Whitmore, W. F., Jr., *Cancer* 1973, 32, 1104. However, this model has been based on histopathologic studies which have significant limitations, and in actuality the sequence of metastatic events remain unknown. Solid tumor animal experiments suggest that only 0.01% of circulating cancer cells eventually create a single metastatic deposit. Fidler et al., *Science* 1982, 217,998–1001; Liotta et al., *Cancer Res.* 1974, 34, 997; Schirrmacher, B., *Adv. Cancer Res.* 1985, 43, 1–32. Ostensibly, a single bone metastasis from human prostatic adenocarcinoma (PAC) could be generated by 10,000 circulating cancer cells (2 cells/1 ml blood). In the past, detection of such a low concentration of cells has been difficult or impossible. Recently, however, Wu et al. used keratin-19 (K-19) mRNA PCR to detect breast cancer micrometastasis in patient lymph nodes and bone marrow. Wu et al., *Lab. Inv.* 1990, 62, 109A. Miyomura et al., also reported the detection of minimal residual acute lymphoblastic leukemia by PCR in patients harboring the Philadelphia chromosome. Miyomura et al., *Blood* 1992, 79, 1366–1370.

A method of detecting the micrometastasis of prostate cancer would be greatly desirable.

SUMMARY OF THE INVENTION

In accordance with the present invention, methods of detecting prostate cancer micrometastasis in a patient are provided comprising the steps of obtaining a sample of RNA from a patient's blood and amplifying said RNA with polymerase chain reaction. The polymerase chain reaction is performed using a pair of primers which are complementary to separate regions of the prostate specific antigen gene. These primers may have the sequences GAGGTCCACACACTGAAGTT (SEQ ID NO: 1) and CCTCCTGAAGAATCGATTCCT (SEQ ID NO: 2). Thereafter, the presence or absence of amplified RNA is detected wherein the presence of amplified RNA indicates micrometastasis of prostate cancer.

DETAILED DESCRIPTION OF THE INVENTION

Figure 1:
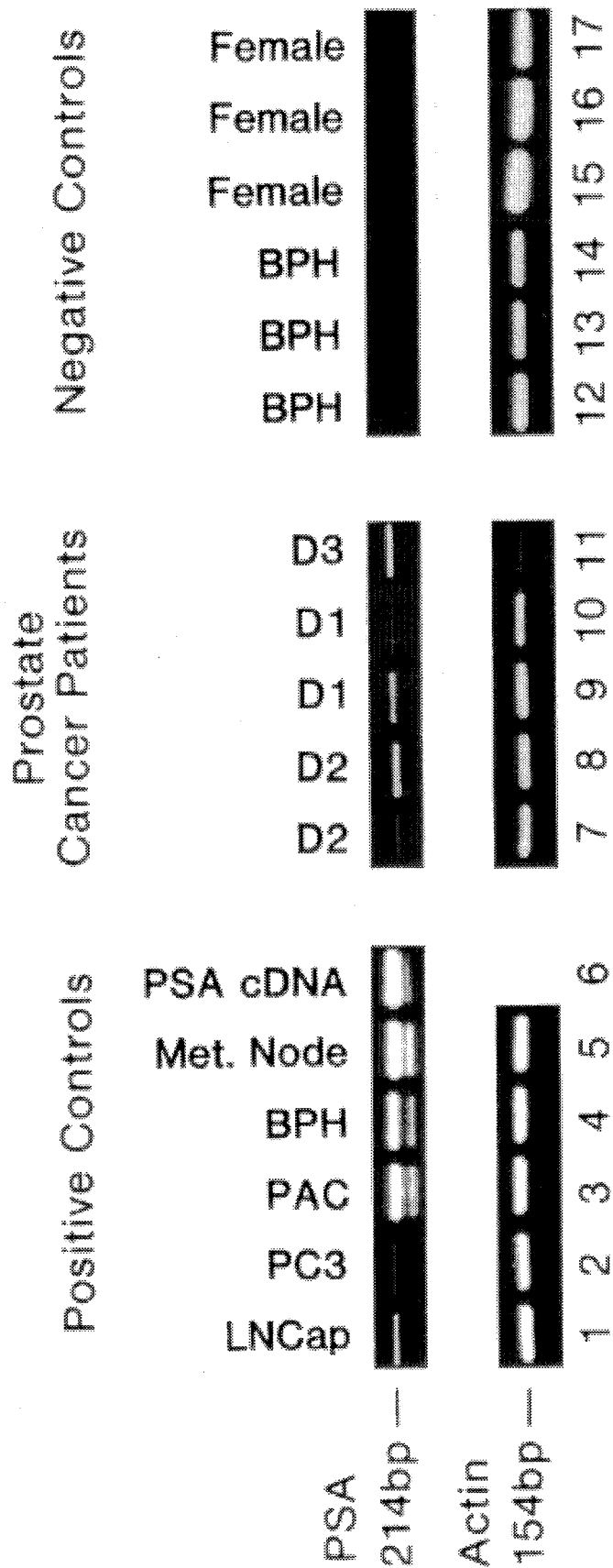
FIG. 1 shows an agarose gel in which micrometastasis is indicated by the presence of a 214 base pair (bp) band.

In accordance with methods of the present invention, methods of detecting micrometastasis of prostate cancer in a patient is provided comprising the step of obtaining a sample of RNA from the patient's blood. Preferably the RNA is obtained from a blood sample such as a peripheral venous blood sample. A whole blood gradient may be performed to isolate nucleated cells and total RNA is extracted such as by the RNazole B method (Tel-Test Inc., Friendswood, Tex.) or by modification of methods known in the art such as described in Sambrook et al., *Molecular Cloning: A Laboratory Manual* (Cold Spring Harbor Laboratory, Cold Spring Harbor, N.Y., 1989).

Thereafter, a polymerase chain reaction may be performed on the total extracted RNA. Preferably a reverse transcriptase PCR amplification procedure may be performed in order to quantify the amount of mRNA amplified. Polymerase chain reaction methodologies are well known in the art. Innis et al., *PCR Protocols,* Academic Press, Inc., San Diego Calif., 1990. Polymerase chain reaction primers may be designed to be complementary to separate regions of the prostate specific antigen (PSA) gene. Henttu et al., *Biochem. Biophys. Res. Comm.* 1989, 160, 903–910. By separate regions is meant that a first primer is complementary to a 3' region of the PSA gene and a second primer is complementary to a 5' region of the PSA gene. Preferably, the primers are complementary to distinct, separate regions and are not complementary to each other.

PSA is an important marker produced exclusively by prostatic epithelial cells and almost always expressed by prostate cancer. Stamey et al., *J. Urol.* 1989, 141, 1076–1083. Thus, PSA2 (5-GAGGTCCACACACTGAAGTT, SEQ ID NO: 1) and PSA3 (5-CCTCCTGAAGAATCGATTCCT, SEQ ID NO: 2) oligonucleotide primers were designed to have high specificity to the PSA gene. A Gene Bank version-70 (Mountain View, Calif.) search confirmed the specificity of these primers to PSA and not to the human glandular kallikrein (HMGK) gene which has high homology to the PSA gene. Henttu et al, *Biochem. Biophys. Res. Comm.* 1989, 160, 903–910. PSA2 and PSA3 bind sequences that span intron III of the PSA gene such that PCR amplification yields a 360 bp DNA which transcribes into a 214 bp RNA product, thereby eliminating the possibility of false positives from DNA contamination. Oligonucleotide primers may be prepared by methods known in the art such as by standard phosphoramidite chemistry.

(See Sambrook et al., supra). Following amplification, the presence or absence of mRNA amplification product may be detected. Preferably, the PCR product may be run on an agarose gel and visualized using a stain such as ethidium bromide. (See Sambrook et al., supra).

The following examples are illustrative but are not meant to be limiting of the invention.

EXAMPLES

Example 1

Patient Specimens

Selection of cases was based on the following criteria. Prostate cancer patients were chosen for analysis if they had: (1) clinically and/or surgically staged DO-D2 disease (D0 = elevated tumor markers with no demonstrable metastasis, D1 = pelvic lymph node involvement, D2 = disseminated disease usually to bone) without having received prior hormonal therapy and who had an elevated serum PSA, or (2) stage D3 disease (D2 disease that is refractory hormonal therapy) with an elevated PSA. Negative control patients consisted of female volunteers, and patients with benign prostatic hypertrophy (BPH) proven by biopsy or men who were on a BPH study protocol. Patients who had surgical manipulation of the prostate during the previous year were excluded from the study. Positive controls included a lymph node from a patient with known metastatic PAC tissue from pathologically proven BPH and cDNA PSA plasmid. Henttu et al, *Biochem. Biophys. Res. Comm.* 1989, 160, 903–910. The protocol was IRB, The Internal Review Board of Thomas Jefferson University Hospital, approved and written consent was obtained. LNCAP and PC3 human cell lines were obtained from The American Type Culture Collection, (Rockville, Md).

Example 2

Blood Preparation for RNA Extraction

Approximately six ml of venous blood were obtained with a standard venipuncture technique using heparinized tubes. Whole blood was mixed with an equal volume of phosphate buffered saline (PBS) which was then layered over eight ml of Ficoll (Pharmacia Uppsala, Sweden) in a 15 ml polystyrene tube. The gradient was centrifuged at 200 g for 30 minutes at 5° C. The lymphocyte and granulocyte layer (approximately 5 ml) was carefully aspirated and re-diluted up to 50 ml with PBS in a 50 ml tube which was then centrifuged at 1800 g for 20 minutes a 5 ° C. Supernatant was discarded, and the pellet containing nucleated cells was used for RNA extraction using the RNazole B method, as described by the company (Tel-Test Inc., Friendswood, Tex.).

Example 3

Oligonucleotide primers and probes

PSA2 (5-GAGGTCCACACACTGAAGTT, SEQ ID NO: 1) and PSA3 (5-CCTCCTGAAGAATCGATTCCT, SEQ ID NO: 2) oligonucleotide primers were custom designed with high specificity to the PSA gene; a Gene Bank version-70 (Mountain View, Calif.) search confirmed the specificity of these primers to PSA and not to the human glandular kallikrein (HMGK) gene which is 75-85% homology to the PSA gene. Henttu et al, *Biochem. Biophys. Res. Comm.* 1989, 160, 903–910. All primers were synthesized and gel purified by the City of Hope DNA Synthesis Laboratory (Duarte, Calif.). PSA2 and PSA3 bind sequences that span intron III such that PCR amplification yielded a 360 bp DNA and a 214 bp RNA product. Previously published actin PCR primer sequences were used to rule out degraded RNA, and amplification with actin oligonucleotide primers A1 and A2 yielded a 154 bp RNA and a 250 bp DNA product. Ben-Ezra et al., *J. Histochem Cytochem.* 1991, 39, 351–354.

Example 4

Polymerase Chain Reaction

The reverse transcriptase reaction and PCR amplification were performed sequentially without interruption in a Perkin Elmer 9600 PCR machine (Emeryville, Calif.). 400 ng of total RNA in 20 µl DEPC (Diethyl-pyrocarbonate) treated water were placed in a 65° C. water bath for five minutes then quickly chilled on ice immediately prior to the addition of PCR reagents. The 50 µl total PCR volume consisted of 2.5 units Taq polymerase (Perkin Elmer, Emeryville, Calif.), 2 units AMV reverse transcriptase (Boehringer Mannheim, Indianapolis, Ind.), 200 µM each of dCTP, dATP, dGTP, and dTTP (Perkin Elmer, Emeryville, Calif.), 18 pM each primer, 10mMTris-HCL, 50 mMKCl, 2 mMMgCl$_{22}$ (Perkin Elmer, Emeryville, Calif.). PCR conditions were as follows: cycle 1 was 42° C. for 15 minutes, then 97° C. for 15 seconds (one cycle); cycle 2 was 95° C. for one minute, then 60° C. for one minute and 72° C. for 30 seconds (15 cycles); cycle 3 was 95° C. for one minute, then 60° C. for one minute, and 72 degrees for one minute (10 cycles); cycle 4 was 95° C. for one minute, then 60 for one minute and 72° C. for two minutes (8 cycles); cycle 5 was 72° C. for 15 minutes (one cycle); and the final cycle was a 4° C. hold until sample was taken out of the machine. The 50 µl PCR products were concentrated down to 10 µl with vacuum centrifugation and the entire sample was then run on a thin three percent Tris-borate-EDTA (TBE) agarose gel containing ethidium bromide. All specimens were analyzed at least twice to confirm a positive or negative outcome.

The potential risk of false positives from cross contamination was avoided by performing RT PCR in a single tube without interruption and using filtered pipet tips. Sensitivity was enhanced by using high amounts of Taq polymerase, progressively increasing extension times, and analyzing the entire 50 µl PCR product on thin ethidium bromide agarose gels. These measures ensured a high fidelity assay while maintaining technical simplicity.

Prostate human tissue specimens, tissue culture cell lines and a PSA cDNA plasmid, cloned and described by Henttu and Vihko; Henttu et al., *Biochem. Biophys. Res. Comm.* 1989, 160, 903–910, were used as positive controls, and they demonstrated the 214 bp bands as shown in FIG.1 top panel. A pelvic lymph node with metastatic PAC, a primary prostate cancer, and a BPH specimen all produced strong PSA PCR signals. The LNCAP and PC-3 human prostate cell lines produced weaker signals.

EXAMPLE 5

Sequencing

Specificity of these primers to the PSA gene was confirmed with DNA sequence analysis of the amplified 214 bp fragment (FIG. 1 Negative Controls) which in this segment had very little homology to the HMGK gene. The 214 bp product was purified with a Qiagen PCR Product Purification kit (Qiagen, Chatsworth, Calif.) as described by the manufacturer. One microgram of the PCR product underwent a PCR sequencing reaction by using the Taq DyeDeoxy Terminator Cycle sequencing kit in a Perkin-Elmer 9600 PCR Machine, as described by Applied Biosystems (Applied Biosystems, Foster, Calif.). The sequenced product was purified using centri-sep columns (Princeton Separations, Adelphia, N.J.) as described by the company. This product was then analyzed with a ABI Model 373A DNA sequencing system (Applied Biosystems, Foster, Calif.) integrated with a Macintosh IIci computer.

Example 6

Detection of Circulating Hematogenous

Micrometastasis

Twelve prostate cancer patients and 17 control patients underwent RT PCR analysis on PSA and actin RNA extracted from blood, as described in Examples 1 through 4 All cases demonstrated satisfactory RNA quality by actin PCR (FIG. 1, bottom row). Of the 12 human prostatic adenocarcinoma (PAC) patients with metastatic disease, four cases (33%) had positive PSA signals indicating the presence of prostatic epithelial cells in the peripheral venous blood. These four cases consisted of two stage D1 patients, one stage D2 patient, and one stage D3 patient (N=1) (FIG. 1, top row). The 17 negative controls, which consisted of eight volunteer women and nine men with BPH, all had undetectable PSA mRNA by RT PCR. These data indicate that RT PCR of the PSA RNA gene can be used to specifically detect circulating hematogenous micrometastasis in patients with stage D1-D3 pathology. These findings are in agreement with studies by Hamby et al. who detected circulating PSA positive cells in patients with metastatic prostate cancer by flow cytology and immunohistology. Hamdy et al., *Br. J. Urol.* 1992, 69,392-396.

Micrometastasis was not detected in eight of twelve prostate cancer patients consisting of two stage D3 patients, two stage D1 patients, and four stage DO patients. In order to enhance the detection of micrometastasis, analysis may focus on buffy coat cells. Results indicate that the prostate cancer cells may be more concentrated in the "buffy coat". The PSA signal was stronger in the RNA extracted from cells obtained only from the "buffy coat" (FIG. 1, lane 8) compared to those isolated from the entire Ficoll layer (FIG. 1, lane 7) in the same prostate cancer patient. These findings are in agreement with those of Harty et al. who found that prostatic epithelial cells migrate into the "buffy coat". Harty et al., *J. Surg. Res.* 1979, 26, 411–416.

---

---

What is claimed is:

1. A method of detecting prostate specific antigen positive cells in a patient having stage D1, D2, or D3 prostate cancer comprising: obtaining a sample of RNA from a patient's peripheral venous blood; reverse transcribing said RNA into DNA;

amplifying said DNA with polymerase chain reaction using a pair of primers which are complementary to separate regions of the prostate specific antigen gene which do not hybridize to human glandular kallikrein gene; and detecting the presence or absence of amplified DNA wherein the presence of amplified DNA indicates the presence of prostate specific antigen positive cells in said patient.

2. The method of claim 1 wherein said primers have the sequences GAGGTCCACACACTGAAGTT (SEQ ID NO: 1) and CCTCCTGAAGAATCGATTCCT (SEQ ID NO: 2).

3. The method of claim 1 wherein said RNA is obtained from cells from the buffy coat of the Ficoll layer of a prepared blood sample.

4. A method of detecting prostate specific antigen positive cells in a patient having prostate cancer comprising:

obtaining a sample of RNA from a patient's peripheral venous blood;

reverse-transcribing said RNA into DNA;

amplifying said DNA with polymerase chain reaction using a pair of primers which are complementary to separate regions of the prostate specific antigen gene which do not hybridize to human glandular kallikrein gene; and detecting the presence or absence of amplified DNA wherein the presence of amplified DNA indicates the presence of prostate specific antigen positive cells in said patient.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 20
        ( B ) TYPE: Nucleic
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

GAGGTCCACA CACTGAAGTT      20

( 2 ) INFORMATION FOR SEQ ID NO: 2:

( i ) SEQUENCE CHARACTERISTICS:
        ( A ) LENGTH: 21
        ( B ) TYPE: Nucleic
        ( C ) STRANDEDNESS: Single
        ( D ) TOPOLOGY: Linear ( i v ) ANTI-SENSE: No ( x i ) SEQUENCE DESCRIPTION: SEQ ID NO: 2:

CCTCCTGAAG AATCGATTCC T      21